United States Patent

Govari

(10) Patent No.: US 9,577,656 B2
(45) Date of Patent: Feb. 21, 2017

(54) NARROWBAND ANALOG NOISE CANCELLATION

(71) Applicant: BIOSENSE WEBSTER (ISRAEL) LTD., Yokeam (IL)

(72) Inventor: Assaf Govari, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 0 days.

(21) Appl. No.: 14/625,755

(22) Filed: Feb. 19, 2015

(65) Prior Publication Data

US 2016/0248434 A1    Aug. 25, 2016

(51) Int. Cl.
H03M 1/06    (2006.01)
A61B 5/00    (2006.01)
(Continued)

(52) U.S. Cl.
CPC ............ H03M 1/0636 (2013.01); A61B 5/042 (2013.01); A61B 5/0402 (2013.01);
(Continued)

(58) Field of Classification Search
CPC .... H03M 1/0626; H03M 1/0617; H03M 1/74; H03M 1/066; H03M 1/0624; H03M 1/186; H03M 1/0607; H03M 1/0854; H03M 1/66; H03M 1/808; H03M 1/0863; H03M 7/0993; H03M 3/344; H03M 3/462; H03M 3/436; H04B 1/1036; H04B 1/12; H04B 1/123; H04L 27/2649; H04L 1/0015; H04L 1/20; H04L 1/0017; H04L 1/0026; H04L 1/0109
(Continued)

(56) References Cited

U.S. PATENT DOCUMENTS 2,622,150 A    12/1952 Coulter et al.
3,465,156 A *  9/1969 Peters ................ G02F 2/00
                                                     359/276
(Continued)

FOREIGN PATENT DOCUMENTS

EP    0488410 A1    6/1992
WO    WO 98/52463 A1    11/1998
WO    WO 2012/145571 A1    10/2012

OTHER PUBLICATIONS

Ramos, R. et al. FPGA-Based Implementation of an Adaptive Canceller for 50/60-Hz Interference in Electrocardiography. IEEE Transactions on Instrumentation and Measurement, vol. 56, No. 6, 2633-2640, Dec. 2007.

(Continued)

Primary Examiner — Lam T Mai
(74) Attorney, Agent, or Firm — Louis J. Capezzuto

(57) ABSTRACT

A method, including receiving an input analog signal containing noise at a specific noise frequency and digitizing the input analog signal to form a digitized signal. The method also includes recovering a first amplitude and a first phase of the noise from the digitized signal, and generating an analog correction signal at the specific noise frequency. The analog correction signal has a second amplitude equal to the first amplitude and a second phase opposite to the first phase. The method further includes summing the input analog signal with the analog correction signal to generate an output analog signal.

10 Claims, 3 Drawing Sheets

(51) Int. Cl.
    *A61B 5/04*     (2006.01)
    *A61B 5/0402*     (2006.01)
    *A61B 5/042*     (2006.01)
    *G06K 9/00*     (2006.01)
    *H04B 15/00*     (2006.01)
    *H03M 1/34*     (2006.01)

(52) U.S. Cl.
    CPC ........ *A61B 5/04012* (2013.01); *A61B 5/7203* (2013.01); *G06K 9/0051* (2013.01); *H03M 1/34* (2013.01); *H04B 15/005* (2013.01); *A61B 2562/18* (2013.01)

(58) Field of Classification Search
    USPC .................. 341/118–155; 375/219, 257, 285
    See application file for complete search history.

(56) References Cited

U.S. PATENT DOCUMENTS

| | | | | |
|---|---|---|---|---|
| 5,157,451 A | * | 10/1992 | Taboada | .................. G01S 17/89 348/262 |
| 5,162,861 A | * | 11/1992 | Tamburino | ............... G01C 3/08 348/319 |
| 5,768,166 A | | 6/1998 | Palatnik | |
| 6,041,250 A | | 3/2000 | dePinto | |
| 6,736,061 B2 | * | 5/2004 | Caunter | .................... B65H 5/32 101/227 |
| 6,763,061 B1 | * | 7/2004 | Strait | .................. H04L 27/2649 375/219 |
| 8,134,255 B2 | | 3/2012 | Hatanaka et al. | |
| 8,597,196 B2 | | 12/2013 | Kishi et al. | |
| 2003/0002590 A1 | * | 1/2003 | Kaku | ................... H04B 1/1036 375/285 |
| 2011/0066052 A1 | | 3/2011 | Mascarenhas | |
| 2015/0124891 A1 | * | 5/2015 | Hwang | ................. H04L 1/0009 375/257 |

OTHER PUBLICATIONS

Rehman, U. et al. Noise Removal From ECG Using Modified CSLMS Algorithm. International Journal of Electronics, Communication & Instrumentation Engineering Research & Development, vol. 4, Issue 3, Jun. 2014, 53-60.
EP Search Report EP 16 15 6274 Dated July 19, 2016.

* cited by examiner

NARROWBAND ANALOG NOISE CANCELLATION

FIELD OF THE INVENTION

The present invention relates generally to noise cancellation, and specifically to cancellation of narrowband noise such as line pickup.

BACKGROUND OF THE INVENTION

Line pickup is a type of noise that can be especially troubling when the signals which are affected by the pickup are relatively small. For example, signals such as ECG (electrocardiogram) signals may typically be relatively small compared to the line noise picked up by leads acquiring the signals. Methods for reducing the effects of this type of noise are known in the art.

U.S. Pat. No. 6,041,250, to dePinto, whose disclosure is incorporated herein by reference, describes an adaptive line noise detection and cancellation system. The system is stated to have, inter alia, a baseline wander filter, high and low pass filters, and an adaptive line noise canceler. The system is also stated to be able to identify and remove contamination from an ECG signal.

U.S. Pat. No. 8,597,196, to Kishi et al., whose disclosure is incorporated herein by reference, describes a cardiac signal processing apparatus which is stated to include a unit for acquiring, from a heartbeat sensor, cardiac signals relating to heartbeats of a subject. The apparatus is also stated to have a low-pass filter for allowing passage of those cardiac signals having a first predetermined frequency or lower, among the cardiac signals, and a higher harmonic noise acquisition unit for acquiring harmonic signals of low-frequency noise by performing high frequency extrapolation on the signals output from the low-pass filter.

U.S. Pat. No. 8,134,255, to Hatanaka et al., whose disclosure is incorporated herein by reference, describes a noise cancellation circuit. The circuit is stated to have a cancellation signal generation section that generates a cancellation signal which cancels an alternating-current component of a power supply terminal voltage of a digital signal processing circuit section. There is also a synthesis section which synthesizes the generated cancellation signal and a power supply voltage of an analog signal processing circuit section to cancel noise superimposed on the power supply voltage.

An article titled "FPGA-Based Implementation of an Adaptive Canceller for 50/60-Hz Interference in Electrocardiography," published in IEEE Transactions on Instrumentation and Measurement, Vol. 56, No. 6, December 2007, to Ramos et al., is incorporated herein by reference. The article describes an adaptive canceller which uses an adaptive filter.

An article titled "Noise removal from ECG Using Modified CSLMS algorithm," published in International Journal of Electronics, Communication & Instrumentation Engineering Research and Development Vol. 4, Issue 3, June 2014, to Rehman, et al, is incorporated herein by reference. The article refers to an adaptive filter that "mainly" minimizes the mean squared error between a primary input and a reference input.

Documents incorporated by reference in the present patent application are to be considered an integral part of the application except that, to the extent that any terms are defined in these incorporated documents in a manner that conflicts with definitions made explicitly or implicitly in the present specification, only the definitions in the present specification should be considered.

SUMMARY OF THE INVENTION

An embodiment of the present invention provides a method, including:

receiving an input analog signal containing noise at a specific noise frequency;

digitizing the input analog signal to form a digitized signal;

recovering a first amplitude and a first phase of the noise from the digitized signal;

generating an analog correction signal at the specific noise frequency having a second amplitude equal to the first amplitude and a second phase opposite to the first phase; and summing the input analog signal with the analog correction signal to generate an output analog signal.

Typically the noise consists of line noise, and the specific noise frequency is selected from a 50 Hz frequency and a 60 Hz frequency. The method may include deriving the specific noise frequency from a line signal.

In a disclosed embodiment the method includes recovering the specific noise frequency from the digitized signal.

In a further disclosed embodiment the input analog signal includes an intra-cardiac electrocardiogram (ECG) signal.

There is further provided, according to an embodiment of the present invention, apparatus, including:

an analog-to-digital (A/D) converter which is coupled to receive an input analog signal containing noise at a specific noise frequency, and to digitize the input analog signal so as to form a digitized signal;

a signal analyzer which is configured to recover a first amplitude and a first phase of the noise from the digitized signal;

an analog signal generator which is configured to generate an analog correction signal at the specific noise frequency having a second amplitude equal to the first amplitude and a second phase opposite to the first phase; and a summation block which sums the input analog signal with the analog correction signal to generate an output analog signal.

The present disclosure will be more fully understood from the following detailed description of the embodiments thereof, taken together with the drawings, in which:

DETAILED DESCRIPTION OF EMBODIMENTS

Overview

Cardiac procedures typically include acquisition of ECG (electrocardiogram) signals. The ECG signals are low amplitude, high impedance analog signals, and so are prone to picking up external signals, such as noise from the line, which act as narrowband noise on the ECG signals. The narrowband noise signals may be significantly larger in amplitude than the ECG signals. While the noise may be reduced by digitizing an incoming noisy ECG signal, identifying a noise signal in the digitized signal, and subtracting the noise signal from the digitized signal, such a process requires a large dynamic range, most of which is taken up by the noise.

Embodiments of the present invention use a different approach. An input analog signal, containing noise at a specific noise frequency, e.g., noise such as 50 Hz or 60 Hz line noise that is narrowband, is digitized. An amplitude and a phase of the noise are recovered from the digitized signal. In some embodiments the value of the specific noise frequency is also recovered from the digitized signal. The recovered amplitude is used to generate an analog correction signal having the same amplitude as the recovered amplitude, and the same frequency as the noise. However, the phase of the correction signal is set to be opposite to, i.e., 180° out of phase with, the recovered phase.

The input analog signal and the analog correction signal are summed, so generating an output analog signal from which the narrowband noise has been removed.

This approach is particularly effective where the level of the narrowband noise is significantly greater than the level of the analog signal, since the large noise signal may enable the amplitude, frequency, and phase of the noise to be accurately evaluated. For example, in some situations where the noise comprises line noise, the narrowband noise level may be 50 dB or even more compared to the analog signal.

System Description

Figure 1:
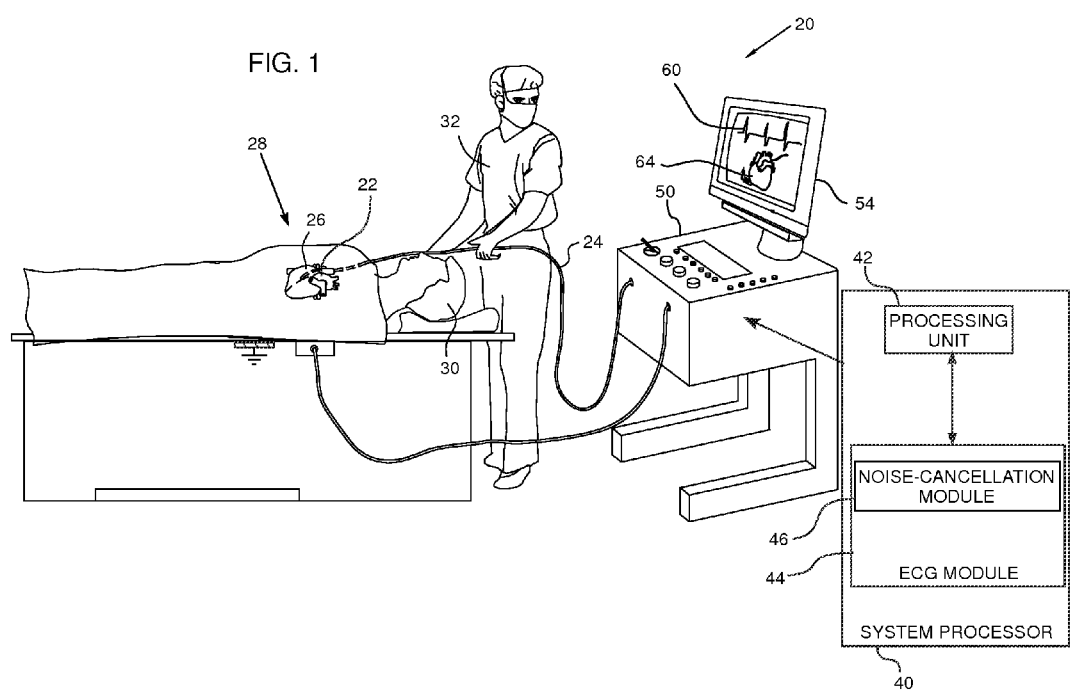
FIG. 1 is a schematic illustration of a narrowband noise cancellation system, according to an embodiment of the present invention.

Reference is now made to FIG. 1, which is a schematic illustration of a narrowband noise cancellation system 20, according to an embodiment of the present invention. System 20 is typically used during a medical procedure on a body organ, and in the description herein the body organ, by way of example, is assumed to comprise the heart, wherein the system is applied to cancel noise on intra-cardiac electrocardiogram (ECG) signals. However, it will be understood that system 20 may be applied to cancel noise on other signals, such as electroencephalograph (EEG) signals.

For clarity, except where otherwise stated, in the following description the signals affected by noise are assumed to be ECG signals, and the narrowband noise on the signals is assumed to be line noise having a frequency of 50 Hz or 60 Hz. In many cases, the narrowband line noise has the same or a greater magnitude than the levels of the ECG signals.

The following description assumes that system 20 senses intra-cardiac ECG signals from a heart 22, using a probe 24. A distal end 26 of the probe is assumed to have an electrode 28 for sensing the signals. Typically, probe 24 comprises a catheter which is inserted into the body of a subject 30 during a cardiac procedure performed by a user 32 of system 20. In the description herein user 32 is assumed to be a medical professional.

System 20 may be controlled by a system processor 40, comprising a processing unit 42 communicating with an ECG module 44. Module 44 in turn comprises a noise-cancellation module 46. Processor 40 may be mounted in a console 50, which comprises operating controls which typically include a pointing device such as a mouse or trackball. Professional 32 uses the pointing device to interact with the processor, which, as described below, may be used to present results produced by system 20 to the professional on a screen 54.

The screen displays results of analysis and processing of ECG signals by ECG module 44. Typically, the resultant ECG signals are presented on screen 54 in the form of a potential vs. time graph, and a schematic example 60 of such a graph is illustrated in FIG. 1. However, the resultant ECG signals may also be used by processor 40 to derive other results associated with the ECG signals, such as a local activation time (LAT). These results are typically presented on screen 54 in the form of a three-dimensional (3D) map 64 of the internal surface of heart 22.

Processor 40 uses software stored in a memory of the processor to operate system 20. The software may be downloaded to processor 40 in electronic form, over a network, for example, or it may, alternatively or additionally, be provided and/or stored on non-transitory tangible media, such as magnetic, optical, or electronic memory.

Processor 40 typically comprises other modules, such as a probe tracking module, a force module that measures a force on distal end 26, and an ablation module that provides regulated to power to electrode 28, or another electrode in the distal end. For simplicity, such modules are not shown in FIG. 1. The Carto® system produced by Biosense Webster, of Diamond Bar, Calif., uses such modules.

Figure 2:
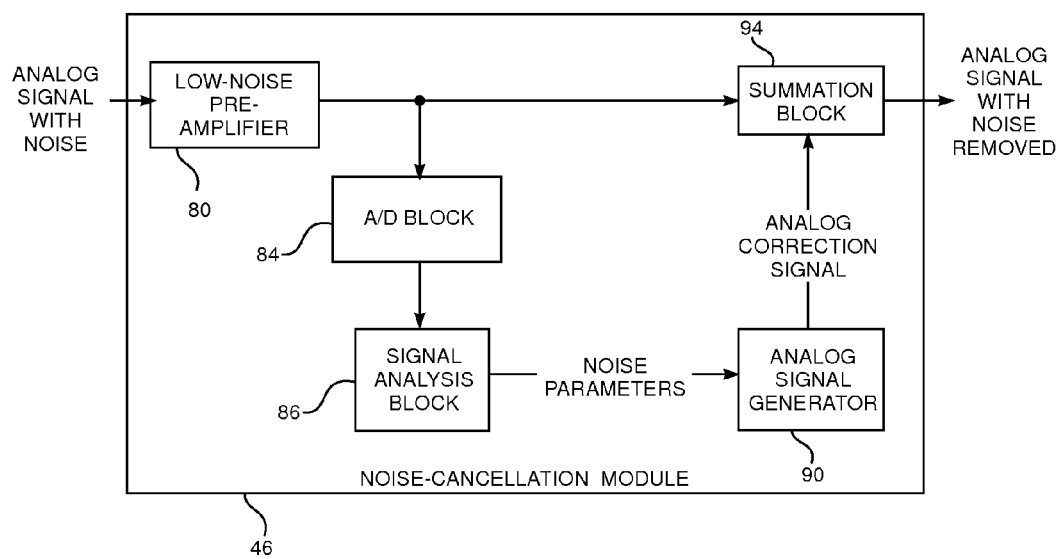
FIG. 2 is a schematic block diagram of a noise-cancellation module, according to an embodiment of the present invention.
Figure 3:
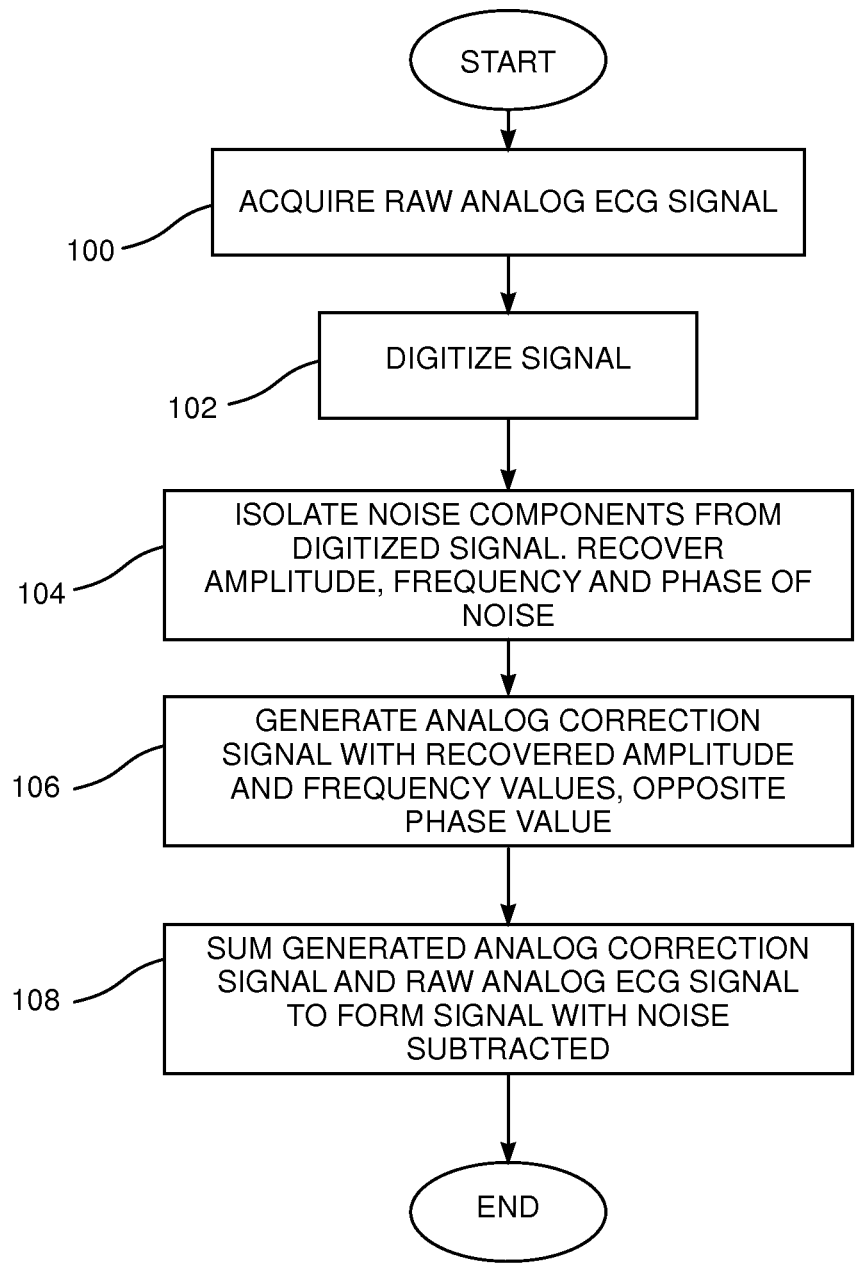
FIG. 3 is a flowchart of actions taken by the module, according to an embodiment of the present invention.

FIG. 2 is a schematic block diagram of noise-cancellation module 46, and FIG. 3 is a flowchart of actions taken by the module, according to an embodiment of the present invention. Module 46 may be implemented in hardware, for example as an application-specific integrated circuit (ASIC) and/or as a field-programmable gate array (FPGA). Alternatively module 46 may be at least partially implemented in software. Module 46 typically comprises a low-noise pre-amplifier 80, which is connected to receive signals from electrode 28. While, for simplicity, pre-amplifier 80 is illustrated as being within module 46, there is no necessity that it is so located. Thus, in a disclosed embodiment, pre-amplifier 80 is incorporated into probe 24, and in some embodiments may be incorporated into distal end 26 of the probe.

The signal received by pre-amplifier 80 is assumed to be a baseband analog signal having a narrowband noise component at a specific frequency. The baseband signal is the ECG signal acquired by electrode 28, upon which has been superimposed line noise of approximately 50 Hz or approximately 60 Hz, corresponding to the narrowband noise component.

The actions performed by the pre-amplifier correspond to an acquisition step 100 of the flowchart, wherein pre-amplifier acquires a "raw" analog ECG signal.

The output from pre-amplifier 80 is digitized by an analog-to-digital (A/D) converter 84, corresponding to a digitization step 102 of the flowchart. The digital output from the A/D converter is transferred to a signal analysis block 86.

The signal analysis block analyzes the digitized signal in order to isolate the narrowband noise component. Typically the analysis comprises performing a Fourier Transform and/or a wavelet transform. The analysis also assumes that an approximate frequency of the narrowband noise is known. The analysis uses the approximate frequency value, assumed to be a nominal value of 50 Hz or 60 Hz, to recover more exactly the specific frequency of the narrowband noise, as well as the amplitude and the phase of the noise.

An analysis step 104 corresponds to the actions performed by the signal analysis block 86. In some embodiments where the narrowband noise comprises line noise, signal analysis block 86 is configured to derive the specific frequency of the narrowband noise from a coupling to the line.

The results of the analysis of the digitized signal are passed to an analog signal generator 90. Generator 90 is configured to generate an analog correction signal having the same values of amplitude and frequency as the values of the narrowband noise amplitude and frequency recovered by the signal analysis block. However, the phase of the analog correction signal produced by generator 90 is configured to be opposite to, i.e., 180° out of phase with, the phase of the narrowband noise. The operation of generator 90, generating the analog correction signal, corresponds to the actions performed in a generation step 106 of the flowchart.

The analog correction signal is transferred to a summation block 94, which is also connected to receive the analog signal output by pre-amplifier 80. Block 94 acts as a mixer, and is configured to sum its two inputs. Because the noise on the output of the pre-amplifier has the same amplitude and frequency, but is opposite in phase to the analog correction signal, summing the two inputs effectively cancels the noise on the incoming analog signal, so that the output signal from block 94 comprises the analog signal with noise removed.

A final summation step 108 of the flowchart, wherein the output from the summation block is the summation of the two input analog signals, corresponds to the operation of summation block 94.

While the description above assumes that the input analog signal is an ECG signal that contains narrowband line noise, it will be appreciated that this type of analog signal, and this type of narrowband noise, are purely exemplary. Thus, embodiments of the present invention comprise other types of analog signal, such as EEG (electroencephalograph) signals, as well as other types of narrowband noise, such as narrowband noise generated by alternating magnetic fields.

It will thus be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

I claim:

1. A method for cancelling noise in a medical system, the method comprising the steps of:
    providing a medical system comprising (i) an analog-to-digital (A/D) converter which is coupled to receive an input analog signal containing noise at a specific noise frequency, (ii) a signal analyzer, (iii) an analog signal generator which is configured to generate an analog correction signal, and (iv) a summation block which sums the input analog signal with the analog correction signal to generate an output analog signal;
    receiving an input analog signal containing noise at a specific noise frequency at the analog-to-digital (A/D) converter;
    digitizing the input analog signal with the analog-to-digital (A/D) converter to form a digitized signal;
    recovering a first amplitude and a first phase of the noise from the digitized signal with the signal analyzer;
    generating an analog correction signal at the specific noise frequency having a second amplitude equal to the first amplitude and a second phase opposite to the first phase with the analog signal generator; and
    summing the input analog signal with the analog correction signal with the summation block to generate an output analog signal.

2. The method according to claim 1, wherein the noise comprises line noise, and wherein the specific noise frequency is selected from a 50 Hz frequency and a 60 Hz frequency.

3. The method according to claim 2, and comprising deriving the specific noise frequency from a line signal.

4. The method according to claim 1, and comprising recovering the specific noise frequency from the digitized signal.

5. The method according to claim 1, wherein the input analog signal comprises an intra-cardiac electrocardiogram (ECG) signal.

6. Apparatus, comprising:
    an analog-to-digital (A/D) converter which is coupled to receive an input analog signal containing noise at a specific noise frequency, and to digitize the input analog signal so as to form a digitized signal;
    a signal analyzer which is configured to recover a first amplitude and a first phase of the noise from the digitized signal;
    an analog signal generator which is configured to generate an analog correction signal at the specific noise frequency having a second amplitude equal to the first amplitude and a second phase opposite to the first phase; and
    a summation block which sums the input analog signal with the analog correction signal to generate an output analog signal.

7. The apparatus according to claim 6, wherein the noise comprises line noise, and wherein the specific noise frequency is selected from a 50 Hz frequency and a 60 Hz frequency.

8. The apparatus according to claim 7, wherein the signal analyzer is configured to derive the specific noise frequency from a line signal.

9. The apparatus according to claim 6, wherein the signal analyzer is configured to recover the specific noise frequency from the digitized signal.

10. The apparatus according to claim 6, wherein the input analog signal comprises an intra-cardiac electrocardiogram (ECG) signal.

* * * * *